(12) United States Patent
Hougen (10) Patent No.: US 6,500,095 B1
(45) Date of Patent: *Dec. 31, 2002

(54) PORTABLE PERSONAL BREATHING APPARATUS AND METHOD FOR EXERCISING THE LUNGS

(76) Inventor: Everett D. Hougen, 5463 Sugarbush, Flint, MI (US) 48503

( * ) Notice: Subject to any disclaimer, the term of this patent is extended or adjusted under 35 U.S.C. 154(b) by 0 days.

This patent is subject to a terminal disclaimer.

(21) Appl. No.: 09/427,962

(22) Filed: Oct. 27, 1999

Related U.S. Application Data (63) Continuation of application No. 08/973,271, filed on Nov. 26, 1997, now Pat. No. 6,083,141, which is a continuation-in-part of application No. 08/386,375, filed on Feb. 10, 1995, now abandoned.

(51) Int. Cl.[7] .............................................. A63B 23/18
(52) U.S. Cl. ......................................... 482/13; 482/111
(58) Field of Search ............................ 482/13, 93, 111; 600/532, 538–540; 128/202.16, 207.16; 84/330, 386, 377, 456, 93; 116/140, 141; 446/200, 202, 205, 206

(56) References Cited

U.S. PATENT DOCUMENTS

| | | | | |
|---|---|---|---|---|
| 515,637 A | * | 2/1894 | Wilhide | 482/13 |
| 569,777 A | * | 10/1896 | Williams | 84/377 |
| 737,008 A | * | 8/1903 | Nichol | 482/13 |
| 4,062,358 A | * | 12/1977 | Kritzer | 128/205.24 |
| 4,114,616 A | * | 9/1978 | Brawn | 128/202.15 |
| 4,291,704 A | * | 9/1981 | Petty et al. | 600/541 |
| 4,444,202 A | * | 4/1984 | Rubin et al. | 600/538 |
| 4,770,413 A | * | 9/1988 | Green | 482/13 |
| 5,255,687 A | * | 10/1993 | McKenna | 600/532 |
| 5,658,221 A | * | 8/1997 | Hougen | 482/13 |
| 5,890,998 A | * | 4/1999 | Hougen | 482/13 |
| 5,899,832 A | * | 5/1999 | Hougen | 482/13 |
| 5,910,071 A | * | 6/1999 | Hougen | 482/13 |
| 6,083,141 A | * | 7/2000 | Hougen | 482/13 |

FOREIGN PATENT DOCUMENTS

| | | | | |
|---|---|---|---|---|
| FR | 2379291 | * | 9/1978 | 482/13 |

* cited by examiner

*Primary Examiner*—Glenn E. Richmon
*Assistant Examiner*—Victor Hwang
(74) *Attorney, Agent, or Firm*—Howard & Howard

(57) ABSTRACT

A breathing apparatus having a main body with a generally cylindrical inner cavity. The main body has a main aperture for the user to breath into and at least two sets of outer openings. An inner cylinder is coaxially disposed within the inner cavity of the main body and is adapted to move relative to the main body. The inner cylinder has an open end adjacent the main aperture, and at least two sets of inner openings selectively matable with the openings in the main body upon movement of the inner cylinder with respect to the main body. By selecting the appropriate alignment of openings, either resistive, percussive, or pulsing breathing exercises can be performed.

13 Claims, 4 Drawing Sheets

PORTABLE PERSONAL BREATHING APPARATUS AND METHOD FOR EXERCISING THE LUNGS

CROSS REFERENCE TO RELATED APPLICATION

This application is a continuation of application Ser. No. 08/973,271 filed Nov. 26, 1997, now U.S. Pat. No. 6,083,141, which is a continuation-in-part of application Ser. No. 08/386,375, filed on Feb. 10, 1995, now abandoned.

BACKGROUND OF THE INVENTION

The present invention relates to a portable respiratory exercise apparatus providing resistance and intra-trachea bronchial percussion on inspiration and expiration to increase pulmonary efficiency, while improving cilial movement which assists mobilization of intra-bronchial mucous or secretions within the lungs.

Research has shown that by practicing deep abdominal breathing, abdominal muscle pressure and temperature are raised, digestion and absorption of foods are improved and pulmonary efficiency is increased. In addition, taking deep breaths while performing little physical movement causes a superfluous amount of oxygen to be made available. Because the large muscular tissue is not consuming the oxygen an increased oxygen supply is made available for many other body systems, such as the brain and the heart.

Forcible and prolonged inspiration and expiration causes a greater expansion and collapse of the air vesicles (alveoli), especially those deep in the lung tissue. By providing resistance to inspiration and expiration, pulmonary muscles are strengthened and developed, thereby allowing a freer and greater exchange of oxygen and carbon dioxide. Persons suffering from lung ailments, healthy persons, and athletes can all improve their pulmonary efficiency through forcible and prolonged inspiration and expiration against resistance.

Some people are able to take only shallow breaths because they are suffering from lung ailments such as asthma, emphysema, chronic bronchitis, chronic obstructive pulmonary disease, or other ailments which reduce the oxygen/$CO_2$ exchange. Frequently, patients recovering from abdominal surgery experience pain during deep breathing and may therefore restrict their own breathing to shallow breaths. In both of the above situations, recovery is slowed because the patients suffer from reduced exchange of oxygen and carbon dioxide in the tissue. Further, the patients are at risk of developing atelectasis because their lungs are not being fully expanded. Atelectasis is a partial collapse of the lungs, possibly leading to necrosis of the lung alveoli. This exacerbates any ailments from which the patient may be suffering by causing poor oxygen exchange in the lungs and possibly resulting in pneumonia.

Patients with emphysema further suffer from mucous blockages in the lungs. Cilia, tiny hairlike structures in the lungs, become flattened down and clogged by mucous. Vibration of the air during inspiration or expiration can cause vibration of the lungs, lung passages (bronchi), and cilia of the patient. This vibration sometimes provides relief to the patient by bringing the cilia to an upright position and mobilizing the mucous, facilitating the expectoration thereof.

Known respiratory exercisers utilize a ball inside a large tube. A user exhales or inhales through a smaller attached tube, causing the ball to rise proportionally to the rate of airflow. However, these known respiratory exercisers only provide resistance to inspiration or expiration, but not both. Further, the large tube must be maintained in a vertical position in order for the respiratory exerciser to operate correctly. This is inconvenient for persons suffering from lung ailments who may be confined to bed and for athletes who wish to restrict respiratory volume flow during exercise. Still further, this respiratory exerciser does not provide a percussive effect on the user; i.e., a vibration of the air on inspiration or expiration.

Another known respiratory exerciser provides a mask which allows air to be inhaled freely and provides resistance against the expiration of air. The masks do not provide resistance to inspiration and do not provide vibration. Further, the masks are too large to be conveniently portable.

Another respiratory exerciser provides a vibration effect upon expiration. A patient exhales into a tube connected to a conical element loosely supporting a ball. When a patient exhales through the tube, the ball is displaced from the conical element causing an oscillatory movement of the ball, thereby generating a variable pressure opposing the expiration. There are several disadvantages to this device. It does not provide vibration of air during inspiration. It is inconvenient for some patients because it must be maintained at a horizontal position during use. Further, the device provides only varying oscillations in air pressure, rather than a sharp percussion of the air by rapid bursts of air pressure from complete opening and closure of the air passages.

Another respiratory exerciser provides a vibration effect upon either inspiration or expiration by using a pair of adjacent air passageways each containing a reed. Each passageway contains a valve utilizing a coil spring to allow either inspiration or expiration. The compression of each spring can be adjusted to vary the resistance to inspiration and expiration independently. As the patient inhales through one passageway and exhales through the other, air flowing past each reed causes each reed to rapidly vibrate, causing a vibration effect on the lungs of the patient. However, adjustment of the coil spring compression during inspiration and expiration is not convenient. Further, vibration of the air is not as effective as would be a sharp percussion of the air by rapid, complete opening and closure of the air passages.

SUMMARY OF THE INVENTION

The present invention provides a respiratory exercise apparatus which is portable, non-positional, and provides percussion and resistance during inspiration and expiration and pulsing during expiration. The user can select whether to exercise through resistance, percussion, or pulsing. The breathing apparatus has a main body and a movable inner member, which in the preferred embodiment is an inner cylinder. Preferably, both the main body and the inner cylinder have holes and slots for resistance, pulse, and percussion exercises. By rotating the inner cylinder and locking it in place, the desired method of exercise can be selected and performed.

Resistance exercises can be performed by aligning holes in the main body and the inner cylinder. Alignment and locking are accomplished through use of grooves and a locking pin, screw, boss, etc. In the preferred embodiment, the inner cylinder has a plurality of grooves with the grooves being preferably oblong and adapted to receive the locking pin to restrict movement. The oblong grooves allow limited reciprocal movement of the inner cylinder with respect to the main body and prevent rotational movement. This restricted movement allows mating holes to move with respect to one another and automatically vary the resistance as a user inhales and exhales. Alternatively, the inner cylinder can be manually reciprocated to vary the resistance or held in place to maintain a predetermined resistance. In the preferred embodiment, there are several paired holes of varied diameter to give varied resistance. These holes are selected by rotating the inner cylinder, aligning a desired set of holes and locking the inner cylinder in place. In the preferred embodiment, there is a flange that has indicator holes that facilitate easy alignment.

A further resistance exercise can be performed by holding the breathing apparatus generally vertically with the inner cylinder pointing up and exhaling. This will raise the inner cylinder. When the lungs are empty, the inner cylinder automatically drops back into the main body. The user then tries to raise the inner cylinder again by exhaling any remaining air in the lungs. The device is then held with the inner cylinder down, which causes the inner cylinder to automatically drop down. The user then inhales to pull the inner cylinder back into the main body until the lungs are full, which then causes the inner cylinder to drop back down. The exercise is completed by further inhaling to try to raise the inner cylinder.

Percussion exercises can be performed by locking the locking member in a second set of grooves which will align slots in the main body and the inner cylinder. In the preferred embodiment, this groove is formed about the circumference of the inner cylinder to allow limited rotational movement of the inner cylinder with respect to the main body. The user can percuss the lungs by rapidly rotating the inner cylinder while the user inhales and exhales into the main body. Rotation of the inner cylinder moves the slots in the inner cylinder and main body with respect to one another allowing quick bursts of air to enter and exit the users lungs. This provides a strong percussion effect which expands the air vesicles deep in the lungs and loosens mucous blockages in the lungs. Because the present invention provides rapid intermittent complete closure of the airflow in and out of the user's lungs during percussion, a more effective percussion effect is obtained than by merely vibrating the air pressure.

Pulse exercises are performed by aligning the locking device with a longitudinally extending groove. This allows the inner cylinder to reciprocate sufficiently to expose the inner slots. To perform the exercise, the device is held upright, and the user exhales, which causes the inner cylinder to raise, expose the slots, and drop repeatedly. In the preferred embodiment, the inner cylinder is weighted to facilitate the reciprocating action.

In the disclosed embodiments, the respiratory exercise apparatus includes a generally cylindrical main body having at least one main aperture. Although disclosed as cylindrical, in some embodiments, the main body can be non-cylindrical. An inner cylinder is disposed within the main body and can rotate and reciprocate within the main body.

It will be apparent to one of ordinary skill that other embodiments could be used to obtain similar results and objectives and still be within the scope of the invention. With reference to the following Brief Description of the Drawings and disclosure, the invention will be described.

BRIEF DESCRIPTION OF THE DRAWINGS

The above, as well as other advantages of the present invention, will become readily apparent to those skilled in the art from the following detailed description of a preferred embodiment when considered in the light of the accompanying drawings in which.

DETAILED DESCRIPTION OF THE INVENTION

Figures 1, 2, 3:
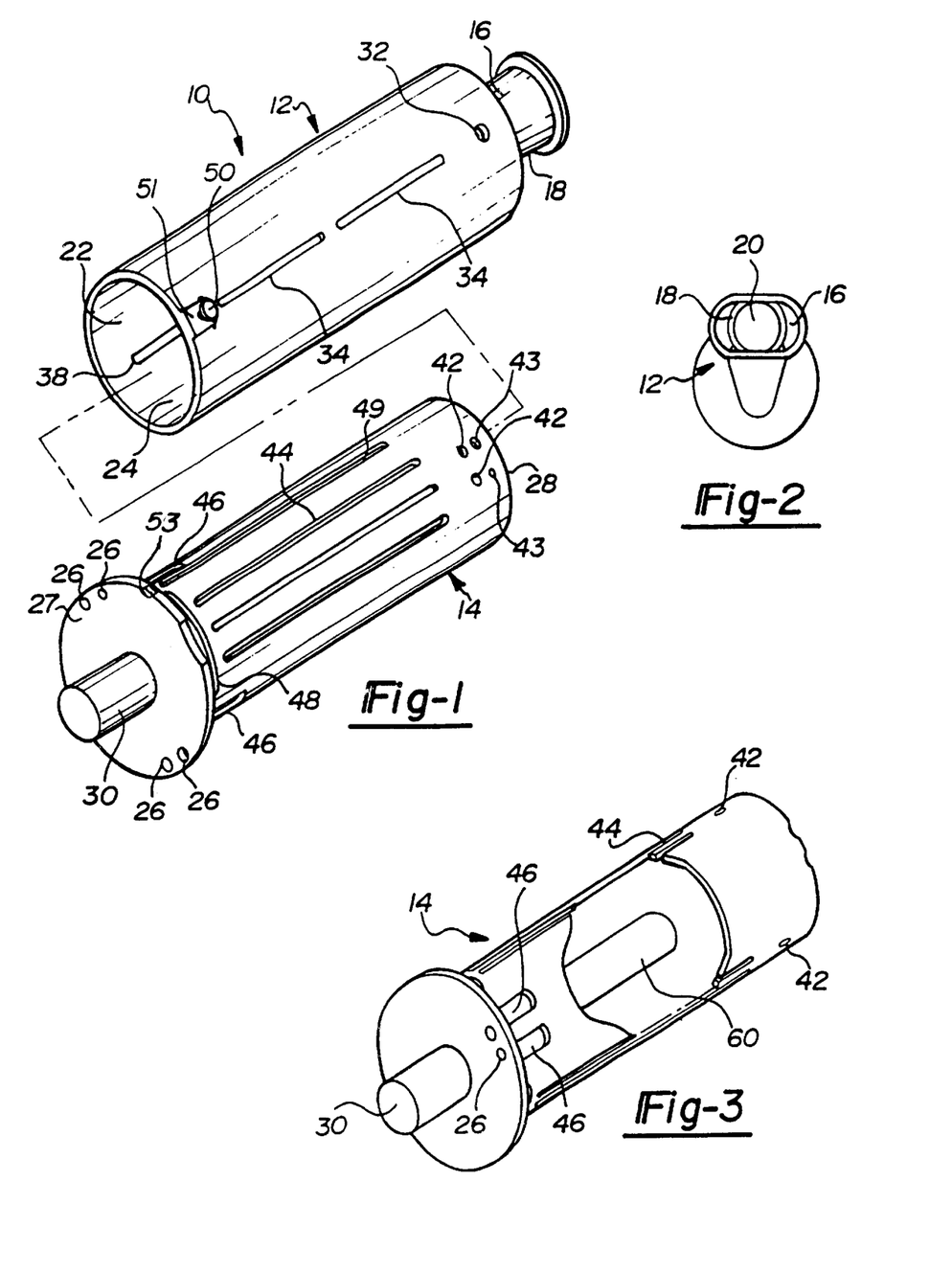
FIG. 1 is a perspective view of a respiratory exercise apparatus in accordance with the present invention.
FIG. 2 is an end view of the respiratory exercise apparatus of the present invention as viewed from the mouthpiece.
FIG. 3 is a partially cut away perspective view of a further embodiment of the present invention.

With reference to FIG. 1, the breathing apparatus of the present invention is generally shown at 10. The breathing apparatus includes a main body 12 and an inner member 14, which is preferably a cylindrical tube. In the illustrated embodiment, the main body 12 is also illustrated as a cylindrical tube, but it should be understood that the shape of the main body 12 could be any desired shape. Further, if the breathing device does not include the percussion exercise, the inner member 14 could be any desired shape which would allow reciprocal movement with respect to the main body 12.

The main body 12 has a mouthpiece 16 attached to a flange 18. The flange 18 is preferably angled at about 45° and includes a bore 20 that communicates with the interior 22 of the main body 12. In the preferred embodiment, the mouthpiece 16 is sufficiently flexible to be stretched over flange 18 to change the angle of the mouthpiece from 45° to generally in line with the main body 12. The opposite end 24 of the main body 12 is open for receipt of the inner cylinder 14. The inner cylinder 14 has a closed end 27 and an open end 28 with the open end 28 being inserted into main body 12. A knob 30 extends from the end 27 so that the inner cylinder 14 can be manually rotated or reciprocated within the main body 12. In the preferred embodiment, the main body is 3.567" long, which includes the mouthpiece 16, and the inner cylinder is 3.67" if the knob 30 is included. The main body and inner cylinder are made of polycarbonate or other moldable plastic, such as polyethylene.

The breathing apparatus 10 is adapted for exercising a users lungs through inspiration and expiration against resistance pulsing and percussion. The apparatus 10 has two sets of openings that can be aligned to provide resistance, pulsing or percussion exercises. By rotating the inner cylinder 14 with respect to the main body 12, the different sets of openings can be aligned and locked in position to allow for a selected exercise.

In the illustrated embodiment, the main body 12 has a hole 32 and a pair of elongated openings or slots 34 and 38 which are about 180° apart. The inner cylinder 14 has a plurality of paired holes 42 and 43 and elongated openings or slots 44 which extend through the inner cylinder 14. These holes 42 and 43 and slots 44 are positioned to align with the holes 32 and elongated slots 34 and 38 respectively as the inner cylinder 14 is rotated with respect to the main body 12. When the holes 42 and 43 are aligned with the hole 32, resistance exercises can be performed. A set of grooves 46 which correspond to the holes 42 are provided in the inner cylinder for holding the inner cylinder 14 with respect to the main body 12. Grooves 46 are adapted to receive a locking member 50 to lock the cylinder in position once an appropriate hole 42 is aligned with hole 32.

When percussive exercises are desired, the slots 34, 38, and 44 are aligned. A different set of grooves 48 are provided, which correspond to the slots 44. Grooves 48 extend circumferentially about the cylinder to restrict movement of the cylinder 14 and main body 12 so that only the slots are aligned for percussive exercises. As will be further described below, the grooves 48 permit limited rotational movement of cylinder 14 with respect to main body 12.

When pulsing is desired, the locking member is inserted into a longitudinally extending groove 49, which extends along the inner cylinder. This groove allows the inner cylinder 14 to reciprocate with respect to the main body 12.

In the disclosed embodiment, the locking member 50 is a small bolt that is threaded into a threaded bore. A raised portion 51 prevents the member 50 from being threaded too far into the grooves. The bolt can be screwed into the groove as desired. It should be understood that other types of locking members could be used, such as a spring loaded detent, a fixed detent, etc.

The grooves 46, which correspond to the holes 32 and 42, are preferably oblong and have their longitudinal axis extending parallel to the longitudinal axis of the inner cylinder 14. Preferably, the locking member 50 has a diameter that is less than the length and width of the groove 46 so that the inner cylinder can reciprocate slightly within the main body 12. Due to the movement of the inner cylinder 14 with respect to the main body 12, the resistance against exhaling can be increased; i.e., the ability to exhale is further restricted, due to the shifting from the hole 42 to the hole 43. When the user inhales, the inner cylinder 14 is pulled back into the main body 12 to shift from hole 43 to hole 42, reducing resistance upon inhalation.

It should be appreciated that by locating the holes 42 and 43 differently, the reverse could be accomplished and greater resistance could be provided when inhaling as opposed to exhaling. Still further, the user can adjust the resistance to inhaling and exhaling by manually sliding the inner cylinder 14 with respect to the main body 12. Again, since the inner holes are sliding with respect to the outer hole 32 in main body 12, the resistance is changed.

In the preferred embodiment, the hole sets 42 and 43 have different diameters to provide varied resistance, depending upon whether the user is exhaling or inhaling. In the preferred embodiment, the diameters of the holes 42 are 0.187", 0.156", 0.125" and 0.093"; the diameters of holes 43 are 0.109", 0.093"; 0.078", and 0.062"; and the diameter of the hole 32 is 0.187". By rotating the cylinder 14, various resistances can be selected and then automatically varied. Further, in the preferred embodiment, there are grooves 46 corresponding to each hole set 42 and 43. Alignment holes 26 are provided in flange 27. These holes 26 correspond in size to their corresponding holes. By locating the holes with the locking member 50, the desired holes 42 and 43 are aligned. Alternatively, by aligning the desired diameter hole 42 with the hole 32, the locking member 50 can be inserted into the adjacent groove. In the disclosed embodiment, there are four (4) sets of holes 42 and 43, four (4) grooves 46 and one hole 32. The holes 42 and 43 are separated into two groups with each set about 180° apart and the hole sets in each group are about 30° apart. The grooves 46 are also separated into two sets with each set about 180° apart and the grooves in each set being about 30° apart. The hole sets 42 and 43 and the grooves 46 are about 90° apart.

With the mouthpiece 16 angled at approximately 45°, the air that escapes from hole 32 blows against the user's face. This provides the user with an indication of the effort being expended and can function as an incentive to continue exhaling effectively.

Percussion is dependent upon grooves 48 which extend between the grooves 46 and correspond to the alignment of the inner slots 44 and the outer slots 34. In the preferred embodiment, each groove 48 extends circumferentially about the inner cylinder through an arc which is greater than 90°. When the locking member 50 is positioned in one of the grooves 48, the inner cylinder 14 can be rotated with respect to the main body 12 through an arc defined by the groove; i.e., approximately 90°. When the inner cylinder 14 is rotated, the slots 44 sweep by the slots 34 to rapidly open and close the slots and rapidly block and open the ingress and egress of air into and out of the breathing apparatus 10. This rapid action causes a percussive result in the users lungs. It should be appreciated by those of ordinary skill in the art that this invention permits percussive exercising of the lungs on inhalation and exhalation.

In the disclosed embodiment, the grooves 48 are positioned apart by about 180°. Each groove is adjacent the end of the slots 44 and extends circumferentially beyond the slots a slight distance to enhance the percussive effect the user receives upon use. Preferably, there are two sets of slots 44 and two grooves 48. Only one set of slots 44 and grooves 48 are shown. Additionally, there are preferably two sets of slots 34 on opposed sides of main body 12. The groove 48 opposite the aligned slot 44 is the groove that receives the locking member 50. It should be appreciated that the groove 48 adjacent the slot 44 could be used if the locking member or the slot 34 were repositioned during manufacture.

In the preferred embodiment, the slots 34 and 44 are long and narrow to give increased percussive effect to the user. The disclosed slots 34 and 44 are approximately two (2) inches long and 0.062 inches wide. For strength, each of the slots 34 and 44 can be formed by two smaller slots positioned end to end. Applicant has found that long narrow slots provide a more effective percussion of the lungs because greater volumes of air can rapidly pass through the slots, and the slots can be closed rapidly, resulting in bursts of air into the lungs. Because of the burst of air, a humming noise is produced, which can also act as an incentive for increased usage. A notch 53 is provided to permit easier alignment of the slots 34 and 44. By aligning notch 53 with locking member 50, the slots are automatically aligned.

To provide pulsing exercise, the groove 49 is aligned with locking member 50. A smaller notch 53 is provided to facilitate proper alignment. By aligning notch 53 with locking member 50, groove 49 is directly beneath locking member 50 and can then receive locking member 50. Groove 49 allows the inner cylinder to reciprocate with respect to the main body 12 as the user exhales. With the unit pointed up, the user exhales and the inner cylinder is raised to expose slots 44. When slots 44 are exposed, the inner cylinder 14 drops down momentarily until pressure from the exhaled air increases in the cylinder 14 to raise it again. This repeated raising and dropping causes a pulsing effect on the lungs.

To use the breathing device, the inner cylinder 14 is rotated with respect to the main body 12 to align either the holes 32 and 42 or the slots 34 and 44 or the groove 49. If resistance exercising is desired, then the holes are aligned. If percussion is desired, then the slots are aligned. If pulsing is desired, then groove 49 is aligned. Once aligned, the locking member 50 is threaded into the adjacent groove. Once the desired exercise is selected, the user inhales and exhales into the mouthpiece 16. If resistive exercising is selected, the inner cylinder 14 reciprocates within the main body 12 to automatically adjust the resistance, or the user can manually control the relative resistance by controlling the amount of reciprocal movement of the inner cylinder 14. If percussion is selected, the inner cylinder 14 is manually rotated by the user as the user inhales and exhales. Knob 30 facilitates rotation of inner cylinder 14 with respect to main body 12. If pulsing is desired, the user uses groove 49.

Figures 4, 5:
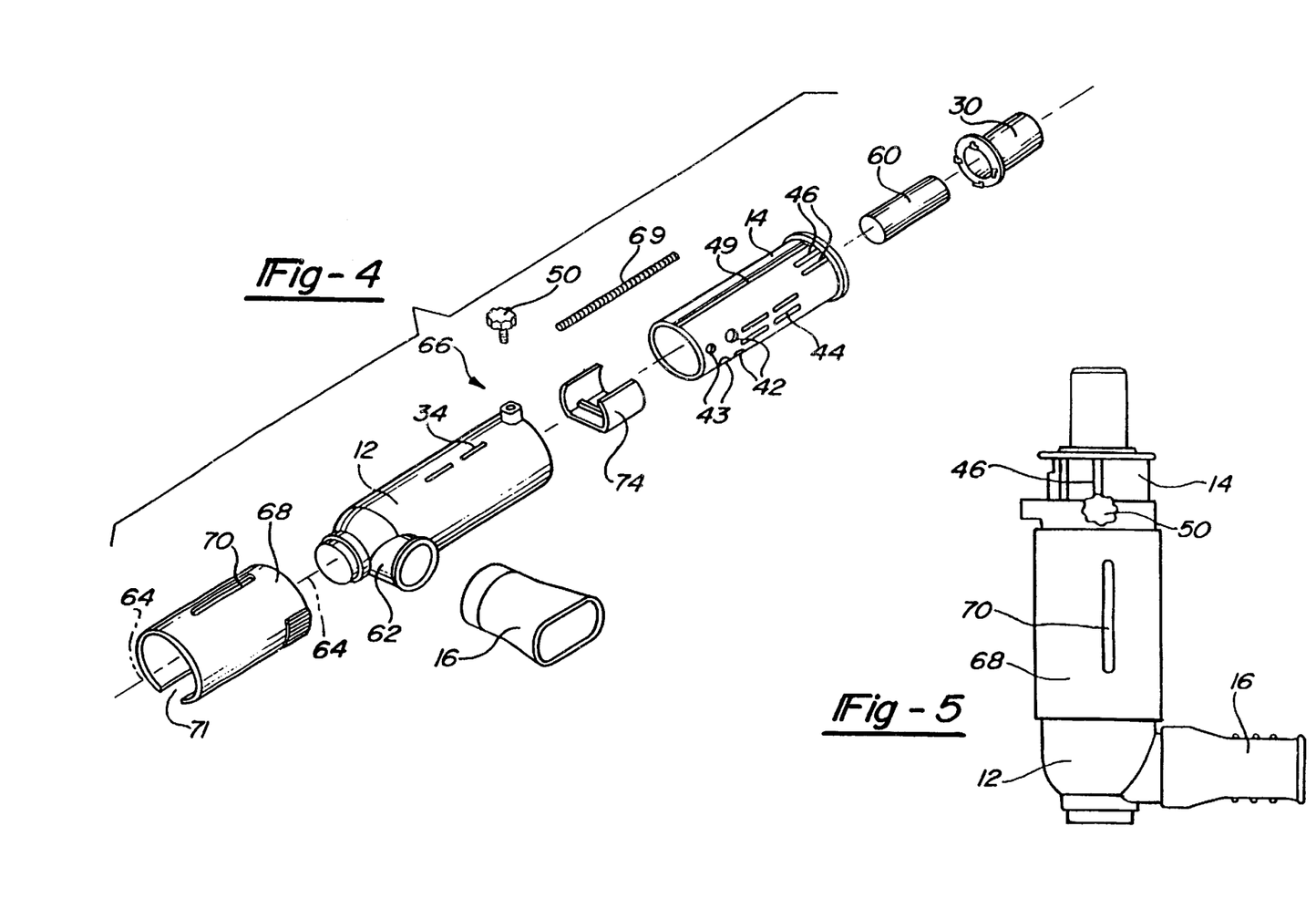
FIG. 4 is an exploded perspective view of a further embodiment of the present invention.
FIG. 5 is a side view of the breathing device of FIG. 4 in the vertical position.

With reference to FIG. 4, a further embodiment of the present invention is shown. In this embodiment, a weight 60 is positioned in the inner cylinder 14. The weight is illustrated as a rod, but it could be a ball, a disk attached to the flange 27, a spring, etc. The weight 60 facilitates the reciprocal movement of the inner cylinder 14 with respect to the main body 12. The weight 60 forces cylinder 14 out of the main body 12 to further restrict inhalation and exhalation or with pulsing to force cylinder 14 back into the main body 12.

With reference to FIG. 4, a further embodiment of the present invention is illustrated generally at 66. In this embodiment, there is a main body 12, an inner member 14 and a mouthpiece 16 as in the previous embodiment illustrated in FIGS. 1 through 3. The main body is about 4 inches long and 1.25 inches in diameter; the inner member 14 is sized to fit into the main body 12. However, breathing device 66 provides for additional exercises as well as the exercises that can performed with the previously described breathing device 10. The inner member 14 has been modified and covers are provided to allow for the additional exercises. Additionally, the mouthpiece 16 is mounted to a short nipple 62 that extends out of the main body 12 at about a 90° angle to the longitudinal centerline 64 of main body 12. The nipple 62 is a ⅞ inch diameter protrusion with a ¾ inch inside diameter. The orientation of mouthpiece 16 at a 90° angle allows the user of the breathing apparatus to twist the mouthpiece 16 on nipple 62 to perform various exercises which will be described more fully below and to vary the resistance when performing these exercises.

As with the previous embodiment, inner member 14 of device 66 is inserted into the end of main body 12 so that it can be reciprocated and rotated with respect to main body 12. A knob 30 extends from the end of inner member 14 to rotate and reciprocate the inner member 14.

In addition to the previously described exercises of resistance, pulsing or bouncing and percussion; breathing device 66 also permits a pumping mode and a slow sustained maximal expiration and inspiration mode. It also includes a spring 69 to enhance the movement of the inner member 14 in the pulsing or bouncing mode. To simplify the description, the same reference numbers will be used to identify the same features found in the previous embodiment. Unless otherwise indicated, the same functions are associated with the same elements. As before, resistance exercises are provided by a lining the thumb screw with grooves 46, of which there are three in this device, with one being out of view. With screw 50 in groove 46 hole sets 42 and 43 are aligned with opening 32 (which is also not illustrated in this figure but is illustrated in FIG. 1). In the preferred, there are three sets of holes 42 and 43 which are sized with a 3:1 ratio in each pair set. The large hole is used for inhaling and the small hole for exhaling. Furthermore, each pair of holes 42 and 43 are of different diameter. In the preferred embodiment, the grooves 46, or which there are three, are approximately ⅝ inches in length. The location grooves 46 align corresponding hole sets 42 and 43 with the exhaust opening 32. In the preferred embodiment, exhaust hole 32 is about ¼ inch in diameter. Percussion exercises are performed by aligning slots 44 with slots 34. In the preferred embodiment, there are two groups of six percussion slots 44 located 180° apart from one another. The slots are preferably ¹⁄₁₆ inch wide by ½ inch long. The slots 34 are in two pairs, 180° apart and are ¹⁄₁₆ inch wide by ½ inch long. A groove 48 is provided in the inner member 14 to accept the thumbscrew 50. Groove 48 is also not shown in this embodiment, since it is out of view; however, it is shown in FIG. 1. When pulsing is desired, the thumbscrew 50 is inserted into groove 49. As before, the inner cylinder 14 reciprocates with respect to the main body 12. As illustrated, a spring 69 is mounted in the groove 49. The thumbscrew 50 when inserted into groove 49 engages one end of the spring and acts against the spring to bias movement of the inner member 14. In this operation mode, the slots 34 and opening 32 in the main body are covered to prevent air from escaping through them. The slots 34 and opening 32 are preferably covered by the inner member 14. However, other methods of covering the openings could be used, such as for example a flexible sleeve 68 that can be snapped over the body member 12. This sleeve 68 can be rotated to close or open slots 34 and opening 32 by aligning the slot 70 and opening 71 or the sleeve 68 over the slots 34 and opening 32. Still further, the main body could be made without the opening 32 and slots 34.

In the pulse mode, the user exhales and the Inner member 14 slides away from body member 12 and compresses the spring 69. The spring provides resistance to the outward movement of the inner member 14. When the openings 1 are exposed from the main body 12, air exhaled by the user escapes through the exposed openings 1 and the inner member 14 snaps back into the main body 12 due to the bias of the spring 69 and the weight 60. In the preferred embodiment, the weight 60 is about 1½ inch in diameter by 1½ inches in length. As the user continues to exhale, movement of the inner member 14 in and out of body 12 occurs very rapidly providing a bounce or pulse action. The snap back action rapidly closes and opens the air passages in the device 66 interrupting the flow of air creating resistance. This pulsing or bouncing action causes a very pronounced change in pressure in the lungs loosening mucous and strengthening the lungs. Preferably in the pulse mode, the user inhales deeply and then exhales into the mouthpiece 16 completely until all bouncing movement stops. The user then inhales deeply and repeats the exercise.

Slow sustained maximal expiration and inhalation can also be performed with this invention. With reference to FIG. 5, by rotating the inner cylinder 14 to align the thumbscrew 50 with one of the grooves 46, the inner member 14 can reciprocate out of main body 12 about ½ inch. As illustrated in FIG. 4, the slots 44 do not extend into the area adjacent the longitudinal extent of grooves 46. In this mode, the only air passage which is open is the air passage created by aligning the openings 42 and 43 with opening 32. If desired, this air passage can be closed by holding a finger over the air passage or by rotating the cover 68 over the passage. If the passage is closed, air can still escape from the device 66, but it is greatly restricted.

In the preferred embodiment, the air passage created by openings 42, 43 and 32 remains open. By using openings 42, 43 and 32, the resistance automatically changes so that the proper resistance is selected to completely fill or empty the lungs. By holding the main body 12 upright in a vertical position, the user can exhale into the mouthpiece and raise the inner member 14. As long as there is sufficient air in the user's lungs to overcome the weight of the inner member 14, in the gravitational pull, the inner member 14 will remain raised. As soon as all sufficient air is expelled from the user's lungs, the inner member will drop back into the body member 12. The resistance can be varied by turning the mouthpiece 16 at a different angle on the nipple 62 and by selecting one of the other grooves 46. By angling the mouthpiece 16, the body member 12 and inner member 14 are angled with respect to the vertical which reduces resistance.

Figures 6, 9, 9A:
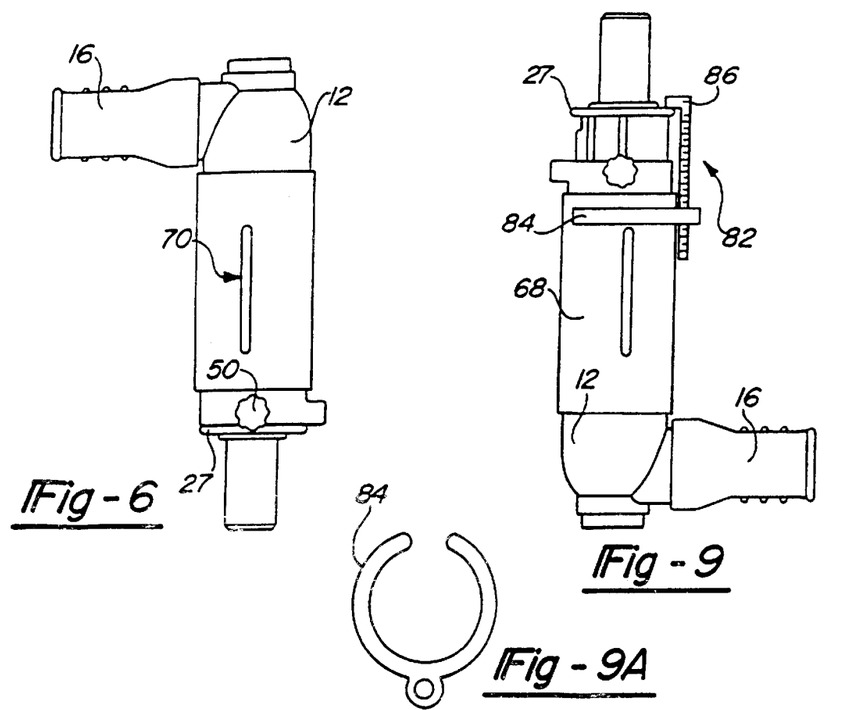
FIG. 6 is a side view of the breathing device of FIG. 5 rotated 180°.
FIGS. 8 through 11 illustrate various flow meters.

By rotating the breathing device 66 180° the inner member 14 points downwardly, see FIG. 6. The user can then inhale completely so that the inner cylinder 14 snaps up into the main body 12. When the lungs are completely filled, the inner member 12 will drop down due to the weight 60 pulling the inner member 14 down. Again, by angling the mouthpiece 16, the resistance can be varied. In this mode the user experiences slow sustained maximal inspiration.

Figure 7:
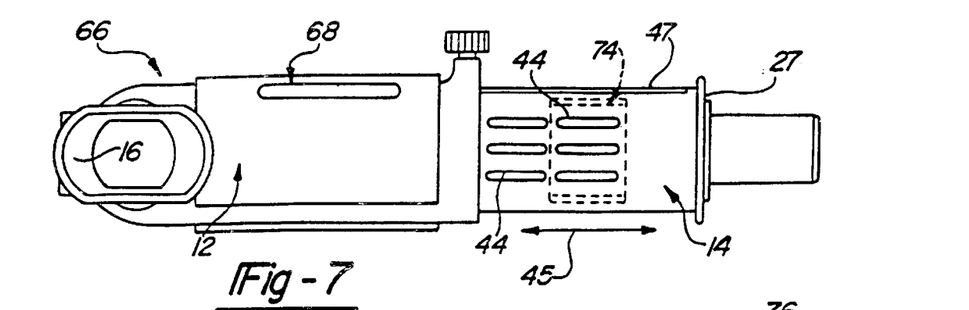
FIG. 7 is a side view of the breathing device of FIG. 4 in the horizontal position.

The other exercise that can be used is the pump mode. In this mode, illustrated in FIG. 7, an internal cover 74 is used to partially cover slots 44 which are adjacent closed end 26 and cover 68 is used to cover slot 34 and opening 32. The breathing device 66 is turned so that body member 12 is generally horizontal. The thumbscrew 50 is inserted into groove 49 or an additional groove 47 could be used, as illustrated in FIG. 7. The user can then reciprocate the inner member 14 with respect to the body member 12 as the user inhales and exhales, see arrow 45 in FIG. 7. As should be appreciated, the mouthpiece 16 is twisted on the nipple 62. The user inhales completely while quickly moving the inner member 14 in and out of the outer member 12. The same is done while the user exhales completely. This mode very effectively maximizes air pressure changes created by the pumping action. This mode provides an effect similar to that achieved in the percussion mode.

Figure 8:
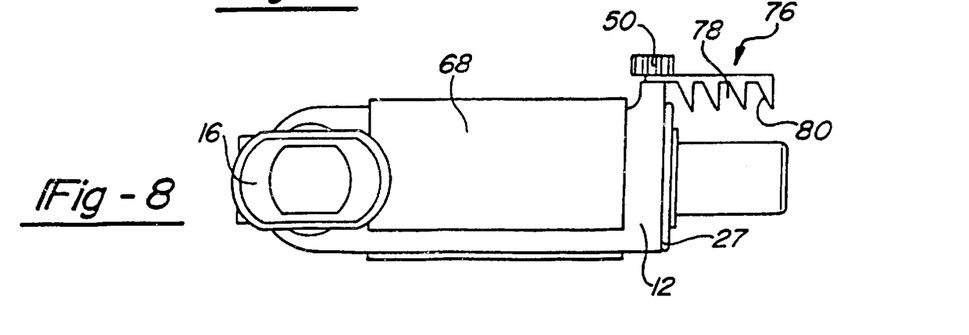

With reference to FIGS. 8 through 11, flow meters or progress meters are illustrated to indicate the amount of air flow and progress a user is making using the breathing devices of the present invention. In FIG. 8, the flow meter 76 attaches onto the end of the body member 12 at the thumbscrew 50. The thumbscrew can be used to hold the meter 76 in position. In the preferred embodiment, flowmeter 76 flexes slightly to allow the inner cylinder 14 to move along the notches 78. The edge of the meter 76 has a plurality of notches 78 with cam surfaces 80. The inner member 14 engages the cam surfaces 80 as it slides out of the body member 12 and gently forces meter 76 back to allow the flange 27 to pass. When the inner member 14 stops sliding out of the inner member 14 it is held by a one of the notches 78. The notches 78 are calibrated to indicate the air flow through the breathing device 66. In the preferred embodiment, the inner member would be rotated to a groove, such as groove 49 (FIG. 1) and the slots 34 and opening 32 would be opened by cover 68 to insure that inner member 14 is not blown out of body 12. The calibration would take into account the flow lost through the open passages.

In FIG. 9, a further embodiment of a flow meter is shown generally at 82. In this embodiment, a guide 84, see FIG. 9a, is snapped onto the body. member 12 with an indicator rod 86 engaging the flange 27. The rod 86 is L-shaped to hook onto flange 27 and includes graduations to indicate the amount of flow and progress. When the user exhales, the rod 86 is moved and remains as the inner cylinder 14 returns.

Figure 10:
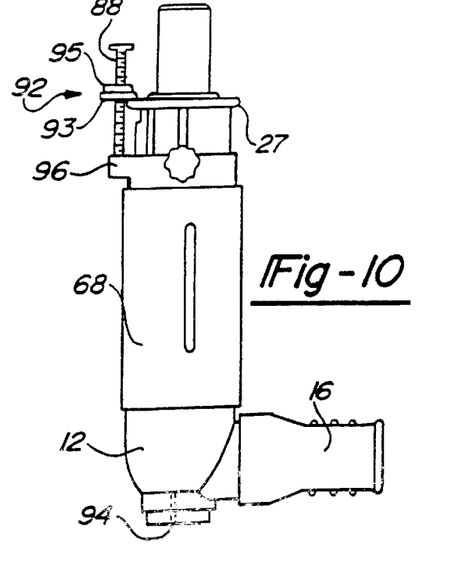

In FIG. 10, a still further embodiment is illustrated. In this embodiment, a removable rod 88 is rigidly mounted into a receptacle 96 formed in the body member 12. Additionally, the rod 88 could be attached to the thumbscrew 50. An indicator 92 is reciprocally mounted about the rod 88. The disclosed indicator 92 is a nylon washer 93 and felt washer 95 which can slide along rod 88. The washers engage the flange 27 and are moved along the rod 88. The felt washer remains to indicate the air flow and progress of the user. In this embodiment, the rod 88 can be inserted into an opening 94 formed in the base of body member 12.

Figure 11:
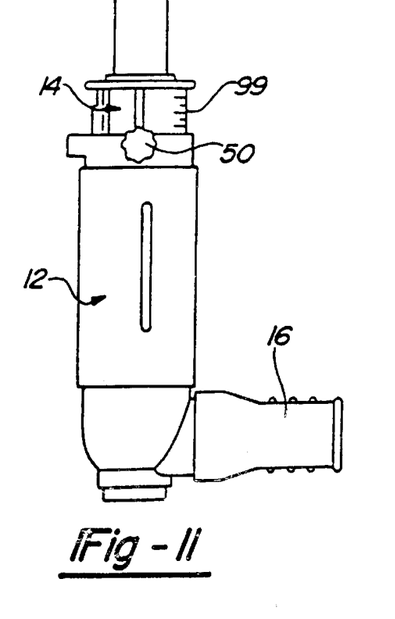

In FIG. 11, another embodiment of a flow meter is illustrated. In this embodiment, the inner member 14 has graduated markings 99. As the user exhales, the mark on the inner member 14 will rise to indicate the air flow and progress. The user will be able to view the height reached and determine flow and progress.

Figure 12:
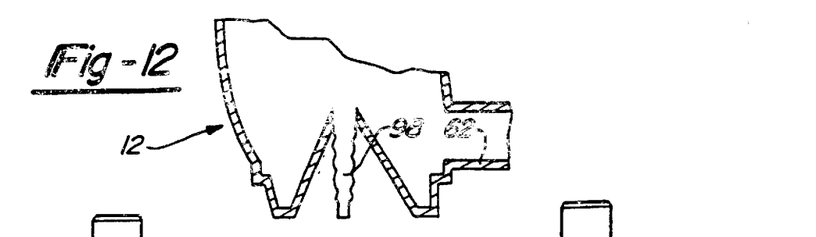
FIG. 12 is a partial cut away view of the breathing device base.
Figure 13:
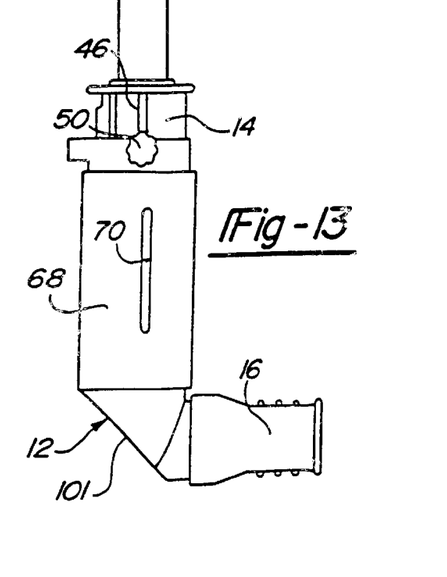
FIGS. 13 and 14 illustrate modified breathing devices having slanted bases.
Figure 14:
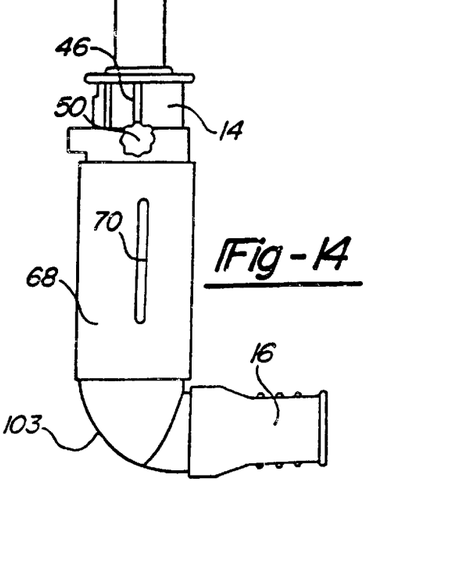

In FIG. 12, an oxygen connector 98 is illustrated. In the disclosed embodiment the connector 98 is inset in body 12 at the same end as nipple 62; however, it could be externally mounted. FIGS. 13 and 14 illustrate further embodiments which have a slanted base 101 in FIG. 13 and 103 in FIG. 14. The slanted base facilitates air flow from mouthpiece 16 through the members 12 and 14.

In accordance with the provisions of the patent statutes, the present invention has been described in what is considered to represent its preferred embodiment. However, it should be noted that the invention can be practiced otherwise than as specifically illustrated and described without departing from its spirit or scope.

What is claimed is:

1. A breathing apparatus comprising:
   a first cylinder having a generally cylindrical first inner cavity and an aperture in communication with said inner cavity, said first cylinder further defining at least one elongated slot therethrough, said at least one elongated slot communicating with said first inner cavity and axially aligned with a longitudinal axis of said first cylinder;
   a second cylinder having a generally cylindrical second inner cavity, said first and said second cylinders telescopically mated one to the other in coaxial fashion and defining a main inner cavity, said first and said second cylinders being rotatable one with respect to the other wherein said second cylinder defines a plurality of elongated slots therethrough, said plurality of elongated slots communicating with said second inner cavity and axially aligned with said longitudinal axis;
   a rotation member affixed to said second cylinder for permitting manual rotation of said second cylinder with respect to said first cylinder, such that rotation of said second cylinder results in alternating alignment and misalignment of said slots of said first and second cylinders to correspondingly result in alternating fluid communication of said main inner cavity with an exterior of said breathing apparatus and blockage preventing said fluid communication of said main inner cavity with said exterior of said breathing apparatus.

2. A breathing apparatus according to claim 1, wherein said first cylinder is a hollow tube defining said first inner cavity and further wherein said aperture is defined at one end of said first cylinder.

3. A breathing apparatus according to claim 2 wherein said aperture is defined by a flange and said apparatus includes a mouthpiece mounted upon said flange whereby a user can inhale and exhale through said mouthpiece.

4. A breathing apparatus according to claim 1 wherein during rotation of said second cylinder with respect to said first cylinder said at least one elongated slot in said first cylinder is sequentially aligned with each of said plurality of elongated slots in said second cylinder such that during each alignment, an exterior of said apparatus is in communication with said main inner cavity.

5. A breathing apparatus according to claim 4 wherein said at least one elongated slot of said first cylinder defines a plurality of elongated slots therethrough.

6. A breathing apparatus according to claim 5 wherein said plurality of elongated slots in said second cylinder are substantially equally spaced about said second cylinder.

7. A breathing apparatus according to claim 6 wherein said plurality of elongated slots in said first cylinder are radially spaced such that when one of said first cylinder elongated slots is aligned with one of said second cylinder elongated slots, each of said first cylinder elongated slots is aligned with one of said second cylinder elongated slots.

8. A breathing apparatus according to claim 7 wherein said at least one elongated slot in said first cylinder is substantially of equal width of each of said plurality of elongated slots in said second cylinder.

9. A breathing apparatus according to claim 8 wherein said second cylinder is rotatable with respect to said first cylinder through an arc greater than 90 degrees.

10. A breathing apparatus according to claim 9 wherein a length of said slots is greater than a width of said slots.

11. A breathing apparatus according to claim 10 wherein said slots have a width of approximately 0.062 inch.

12. A method for exercising the lungs, said method comprising the steps of:

providing a breathing apparatus having a first cylinder defining an inner cavity and an aperture in communication with the inner cavity wherein the first cylinder also defines at least one longitudinally aligned elongated slot in communication with the inner cavity and a second cylinder mated to the first cylinder in a coaxial fashion and rotatable one with the other wherein the second cylinder defines a plurality of longitudinally aligned elongated slots of substantially equal width therethrough and includes a rotation member affixed thereto for permitting manual rotation of the second cylinder with respect to the first cylinder;

inhaling and exhaling into the first cylinder;

rotating the second cylinder with respect to the first cylinder; and intermittently aligning and misaligning said at least one elongated slot in the first cylinder with the elongated slots in the second cylinder such that the rotation of the second cylinder results in alternating fluid communication of the main inner cavity defined by the combined first and second cylinders with an exterior of the breathing apparatus and preventing said fluid communication of said main inner cavity with said exterior of said breathing apparatus to intermittently restrict the ingress and egress of air into and out of the breathing apparatus to provide percussive bursts of air into the lungs.

13. The method according to claim 12 wherein said rotating step includes rotating the second cylinder through an arc greater than 90 degrees.

* * * * *